Figure 1:
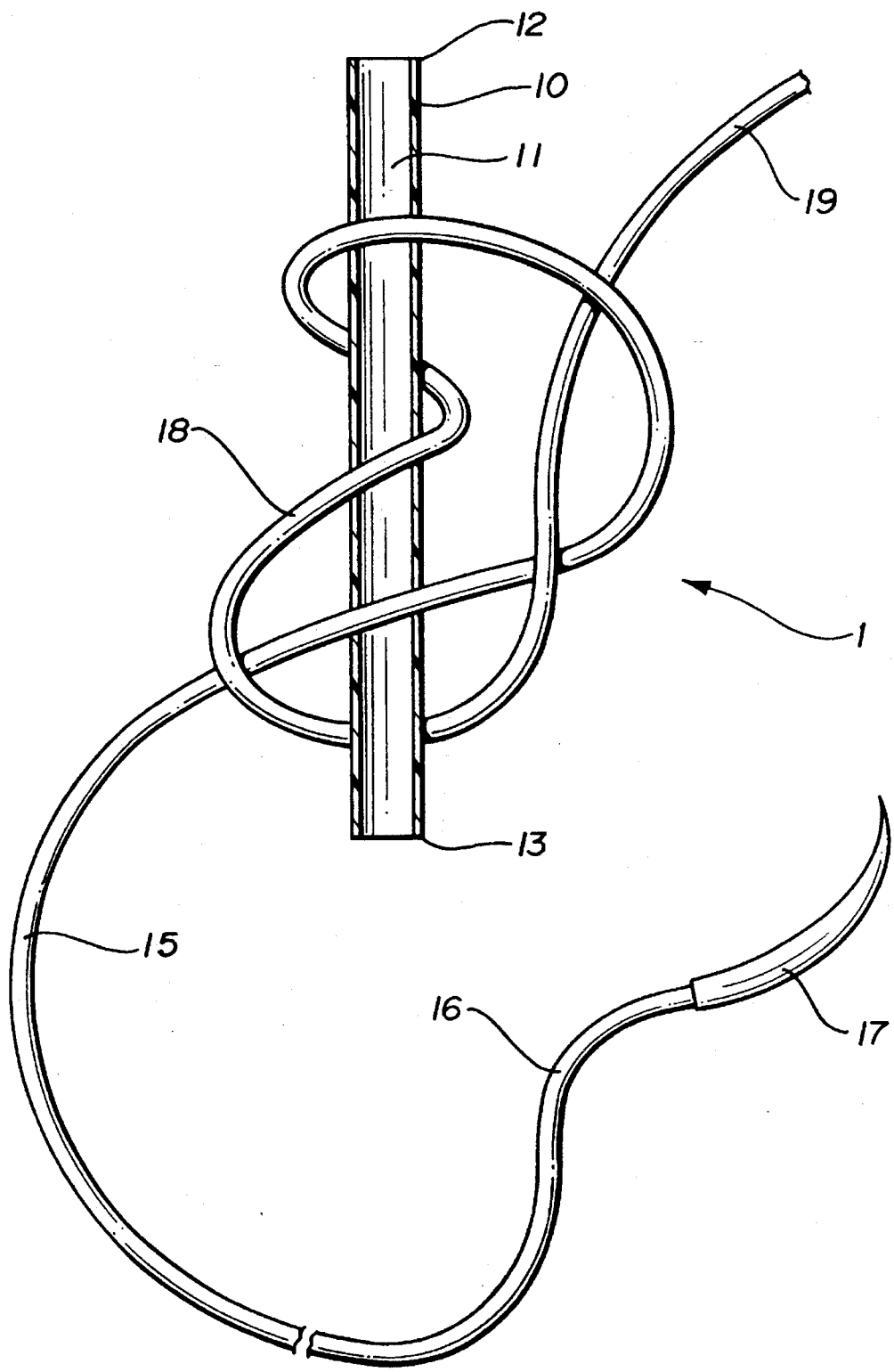

United States Patent [19]

Harm et al.

[11] Patent Number: 5,454,821

[45] Date of Patent: Oct. 3, 1995

[54] SYSTEM FOR THE APPLICATION OF KNOTS IN SURGICAL SUTURE MATERIAL

[76] Inventors: Michael Harm, D-23845, Itzstedt;
Bernard Hinsch, D-22851, Norderstedt;
Christoph Walther, D-24568,
Kattendorf, all of Germany

[21] Appl. No.: 164,046

[22] Filed: Dec. 8, 1993

[30] Foreign Application Priority Data

Dec. 15, 1992 [DE] Germany .......................... 42 43 427.0

[51] Int. Cl.⁶ .................................................. A61B 17/00
[52] U.S. Cl. .............................. 606/148; 606/139; 289/17
[58] Field of Search ..................... 606/139, 144,
606/145–148, 228, 230; 112/80.03, 169;
289/17

[56] References Cited

U.S. PATENT DOCUMENTS

| | | | |
|---|---|---|---|
| 4,018,229 | 4/1977 | Komiya | 606/139 |
| 4,052,988 | 10/1977 | Doddi et al. | 606/228 |
| 5,035,701 | 7/1991 | Kabbara | 606/148 |
| 5,037,433 | 8/1991 | Wilk et al. | 606/139 |
| 5,211,650 | 5/1993 | Noda | 606/148 |
| 5,312,423 | 5/1994 | Rosenbluth et al. | 606/148 |
| 5,334,199 | 8/1994 | Yoon | 606/144 |

*Primary Examiner*—Stephen G. Pellegrino
*Assistant Examiner*—Jeffrey A. Schmidt
*Attorney, Agent, or Firm*—Emil Richard Skula

[57] ABSTRACT

A system for the application of knots in surgical suture material consists of a pre-knotted surgical suture means (1) and a surgical knot applicator. The pre-knotted surgical suture means (1) has a sleeve (10) open at both ends (12, 13) and a surgical suture material (15) such as thread, cord, etc., which suture material is tied around the sleeve (10) to produce a pre-knotted displaceable knot (18) and has a free end (16). The surgical knot applicator contains a shaft, whose distal end-zone comprises an opening corresponding to the diameter of the sleeve (10). The sleeve (10) inserted with its proximal zone (12) into this opening is pulled back into the interior space of the shaft with a pulling-in device. The suture and the knot (18) are pulled tight by moving the free end (16) of the surgical suture material (15) guided through the sleeve (10) in proximal direction (arrow) with a pulling device.

1 Claim, 4 Drawing Sheets

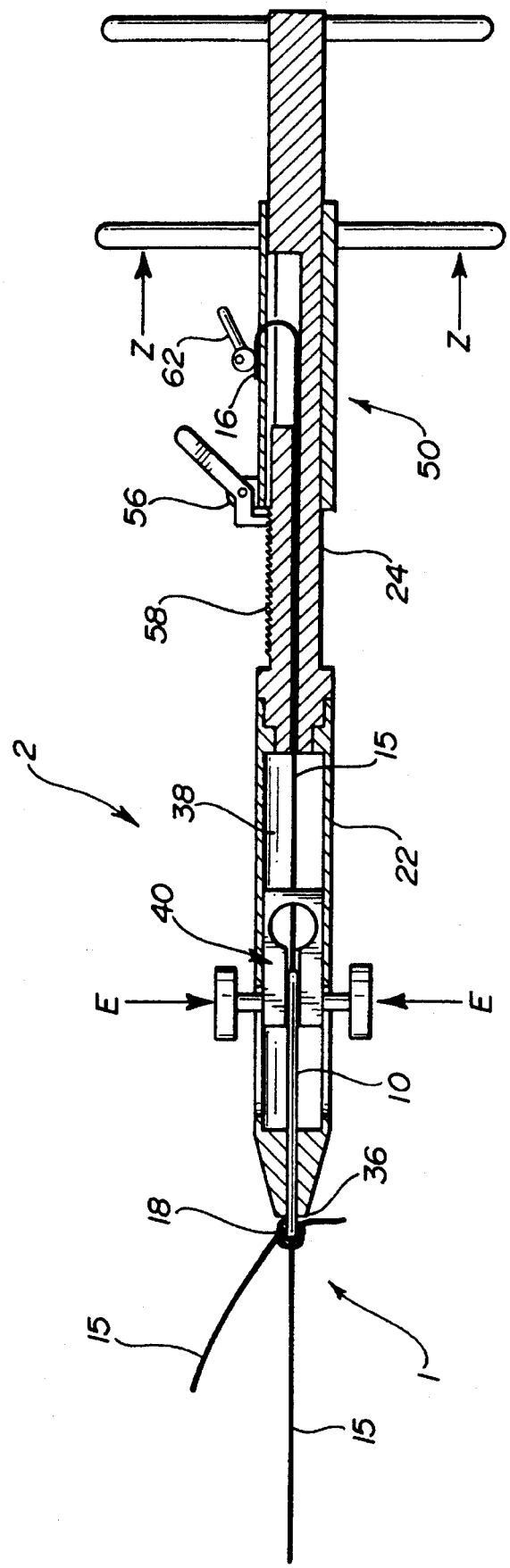

SYSTEM FOR THE APPLICATION OF KNOTS IN SURGICAL SUTURE MATERIAL

The invention relates to a system for the application of knots in surgical suture material.

When sutures are set in surgery, the suture material generally has to be knotted. This is often time-consuming. In an operative field which is accessible only with difficulty, the creation of a knot in surgical suture material is associated with particular difficulties. Use is thus often made of sliding knots which are laid around the suture material in a more readily accessible area and then pushed along the suture material as far as the desired point. However, sliding knots are particularly complex in structure and thus also time-consuming.

Known from endoscopic surgery is a small tube about whose casing surface one end-zone of a surgical thread is pre-knotted to produce a sliding knot. Guided longitudinally displaceable in the inside of the small tube is a flexible metal wire graspable at its proximal end, which wire emerges at the distal end from the small tube and is shaped to form an eyelet. After the thread has been laid around an organ which is to be tied off, for example in order to perform a ligation, its free end is pushed through the eyelet. The eyelet, together with the thread-end, is then moved into the inside of the small tube by pulling on the proximal end of the wire, the thread lying double and the flexible eyelet changing its shape to a smaller extension in the direction transversal to the longitudinal axis of the small tube. The sliding knot can now be displaced in distal direction relative to the small tube until it slides over onto the thread entering the distal tube end. The thread now assumes the position of the small tube relative to the sliding knot, and the resultant ligature loop can be pulled tight by moving the free thread-end in proximal direction.

With this surgical equipment, which is intended only for the production of ligatures, it proves disadvantageous that the thread is folded in the area of the eyelet, which is prejudicial in particular to thicker or intractable suture material. The method of using the equipment is also quite inflexible, since it must be kept as a whole in the vicinity of its area of use if the sliding knot is not to be too remote from its final position before being pulled tight.

The object of the invention is to provide a possibility for the application of knots in surgical suture material in which, especially in open surgery, thicker and relatively inflexible suture material, such as for example .a cord, can also be used and which permits a rapid and reliable application of a knot.

This object is achieved by a system for the application of knots in surgical suture material with the features of claim 1. Advantageous designs result from the dependent claims.

One component of the system according to the invention for the application of knots in surgical suture material is a pre-knotted surgical suture means which has a sleeve open at both ends as well as a surgical suture material such as a thread, a cord, a band etc. The suture material is tied around the sleeve to produce a pre-knotted displaceable knot. A surgical needle can be attached to its free end. Another component of the system according to the invention is a surgical knot applicator with a shaft, the distal end-zone of which shaft has an opening corresponding to the external diameter of the sleeve. If the sleeve is inserted into this opening, it can be pulled into the interior space of the shaft with the help of a pulling-in device. Also provided is a pulling device which serves for the pulling of the free end of the surgical suture material guided through the sleeve in proximal direction.

With the help of the system according to the invention, knots can also be applied in thick and relatively inflexible suture material. Thus, not only threads but also cords are suitable. In a preferred version, a resorbable material is used, namely polydioxanone (PDS; see e.g. DE-OS 40 12 602 and source details quoted there).

When the system according to the invention for the application of knots in surgical suture material is applied, a pre-knotted surgical suture means is first removed from its sterile packaging. If the free end of the surgical suture material is provided with a surgical needle, a suture can be produced in conventional manner. The sleeve with the pre-knotted displaceable knot can lie in the vicinity of the later final position of the knot. Alternatively, the sleeve can also already be inserted into the opening in the distal end-zone of the surgical knot applicator. After the suture has been completed apart from the application of the knot, the needle is cut off and the free end of the surgical suture material is introduced through the sleeve inserted into the opening of the knot applicator into the interior space of the shaft, which can take place for example with the help of a separate gripping instrument. There, the free end can be grasped with the pulling device. The sleeve can now be pulled back into the interior space of the shaft by means of the pulling-in device, until the displaceable knot lies against the distal end-zone of the shaft; at this point the suture material, before its entry into the opening, assumes the function of the sleeve relative to the knot. With the help of the distal end-zone of the shaft, the knot can be directed to its final position, aligned and pressed on. At the same time, the pulling device can be actuated, to pull tight the suture material and thus also the displaceable knot. After the suture has been completed, the pulling device is released in order to move the surgical knot applicator somewhat away from the pulled-tight knot, so that a piece of suture material again emerges from the opening. If the suture material is then severed in the vicinity of the opening, a sufficiently long piece remains in the area of the knot to prevent a loosening of the knot.

The system according to the invention thus makes possible a rapid and reliable application of knots in surgical suture material; the complex and difficult knot-tying processes is dispensed with. The method of use of the system is flexible; thus, for example, the distal end-zone of the shaft can be used in numerous ways to align the knot. It is also up to the surgeon to judge when he inserts the sleeve into the opening at the shaft of the knot applicator. If the free end of the surgical suture material is not fitted with a surgical needle, the system according to the invention can be used to lay a ligature.

Application examples for open surgery are the closure of the sternum (breast bone), the operative treatment of the half-joints of the pelvic girdle (e.g. the restoration of the symphysis and also of the sacro-iliac joint), the operation of the acromioclavicular joint (AC joint) and the fixing of small bone fragments (e.g. in the form of a cerclage). The knot preferably has a small knot volume. This proves advantageous particularly when using thicker resorbable suture material, such as for example a woven or braided cord made from PDS, as it can take more than 100 days before such suture material is decomposed in the body. During this period, a knot with a small volume naturally hampers the progress of the healing process less than a large knot. A Weston-style clinch knot, which combines a small knot volume with a large holding strength or knot-tearing strength, is particularly suitable.

In a preferred version, the pulling device of the surgical knot applicator, which for example comprises a ratchet, is provided with a device for limiting the pulling force, which device can also be fitted with a device for adjusting the desired pulling force. The effect of this is that, when the surgical suture material guided through the sleeve is pulled, the desired pulling force is not exceeded, which reliably prevents a tearing of the suture material. If, upon operation of the surgical knot applicator, the suture material is pulled in until the device for limiting the pulling force responds, the suture and the knot can be closed with a precisely defined force which is best matched to the purpose in question. Thus, for example, all six sutures which are customarily laid upon closure of the sternum with resorbable suture material can be pulled thight with the same force, which promotes the healing process. - The device for limiting the pulling force can, for example, also comprise an adjustable, pneumatic pressure cylinder.

The opening is preferably provided in the distal front side of the knot applicator and enclosed by an annular shoulder. The shaft can be sloped in its distal end-zone onto the periphery of the annular shoulder. This configuration of the shoulder makes possible an easy and simple alignment and pressing-on of the knot without damaging it in the process. The distal end-zone of the shaft can also have a round or oval or other shape in order to be best matched to the anatomical circumstances. Where appropriate, it can also be designed as a replaceable end-piece in order to provide a given knot applicator with a variable configuration.

The pre-knotted surgical suture means is preferably provided in sterile packaging independently of the surgical knot applicator. One and the same surgical knot applicator can thus be used with numerous pre-knotted surgical suture means which can also differ with regard to the suture material type and type of knot. The advantages of the system according to the invention for the application of knots in surgical suture material can thus be exploited at low expense in various ways which are best matched to the type of operation in question.

Figure 2:
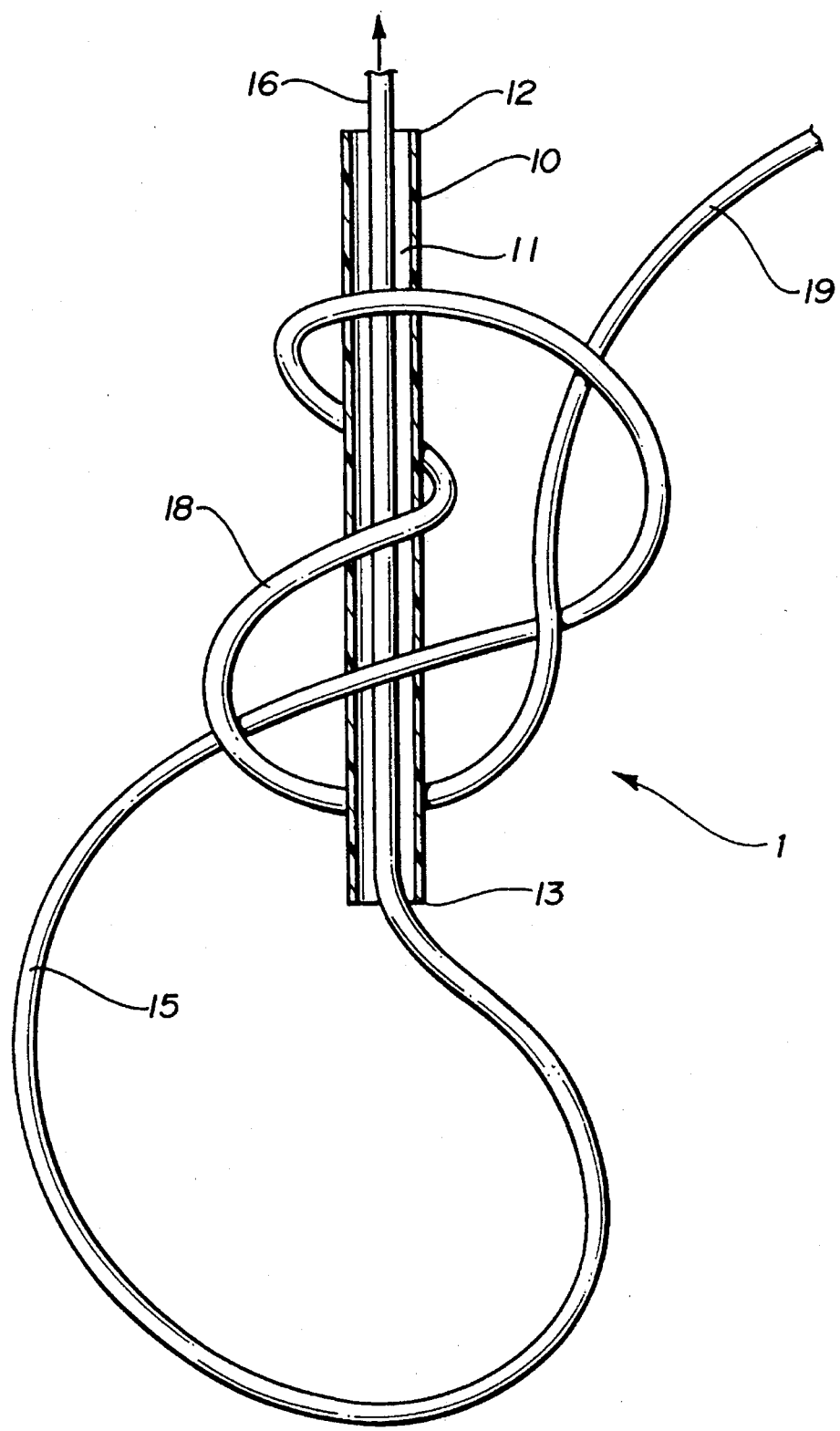
Figure 3:
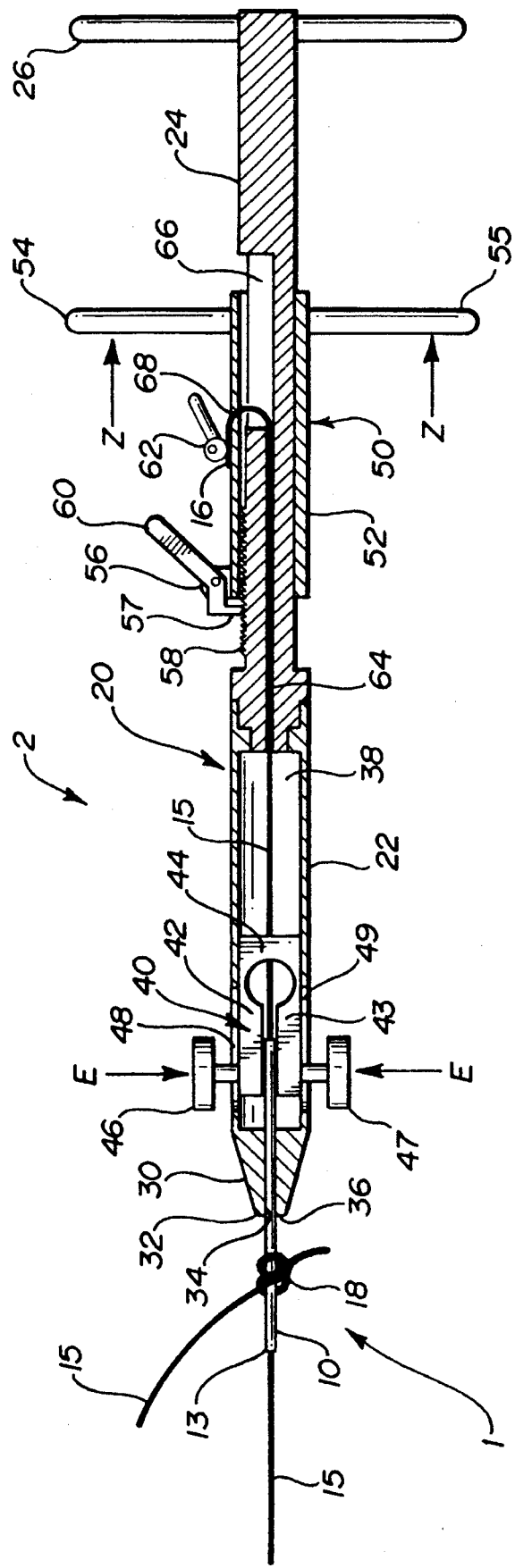

The invention is described in more detail below with reference to an embodiment. The drawings show:

FIG. 1 a diagrammatic view of a pre-knotted surgical suture means with a surgical needle at the free end of the surgical suture material, FIG. 2 a diagrammatic view of the pre-knotted surgical suture means from FIG. 1 after the cutting-off of the surgical needle and after the introduction of the free end of the surgical suture material into the sleeve, FIG. 3 a longitudinal section of a surgical knot applicator having the sleeve of a pre-knotted surgical suture means inserted into the opening in the distal end-zone, the free end of the surgical suture material being guided through the sleeve and secured to a pulling device, and FIG. 4 a longitudinal section of the surgical knot applicator represented in FIG. 3, the sleeve being largely retracted and the free end of the surgical suture material being pulled in proximal direction.

FIG. 1 shows, in diagrammatic representation, a pre-knotted surgical suture means 1 of the system according to the invention for the application of knots in surgical suture material. The pre-knotted surgical suture means 1 comprises a preferably cylindrical sleeve 10 which is open at the proximal end 12 and at the distal end 13, so that its interior space 11 is accessible. The sleeve 10 can also be longer, relative to its diameter, than represented in FIG. 1, compare for example FIG. 3. Another constituent of the pre-knotted surgical suture means is a surgical suture material 15, such as e.g. a thread or a cord made from a material which is suitable for surgical purposes. A surgical needle 17 can be secured to the free end 16 of the surgical suture material 15. The other end-zone of the surgical suture material 15 is bound around the sleeve 10 as a pre-knotted displaceable knot 18. An end-zone 19 prevents a loosening of the knot.

The knot shown in FIG. 1 is the initial stage of a Weston-style clinch knot, as described in Peter V. Weston, "Instruments and Methods", Vol. 78, 144 et seq. (1991). The better to illustrate the guiding of the surgical suture material 15, the knot loops are drawn loosened; in reality, they lie close against the sleeve 10. A complete Weston-style clinch knot is formed when the free end 16 of the surgical suture material 15 is guided, after the cutting-off of the surgical needle 17, via the opening at the distal end 13 through the interior space 11 of the sleeve 10, see FIG. 2, and the sleeve 10 is then retracted in the direction of the arrow drawn in FIG. 2. The knot 18 slides without difficulties over the preferably smooth surface of the sleeve 10 and is still displaceable even if it passes over onto the surgical suture material 15 after the sleeve 10 has been pulled back. If the knot 18 is held in its spatial position with the help of the knot applicator described below, the loop shown in FIG. 2 made from surgical suture material 15 can be pulled tight by pulling the free end 16 in the direction of the arrow. The Weston-style clinch knot is distinguished by its secure hold. Further advantages are its small knot volume and its small tendency to open of its own accord.

Instead of the Weston-style clinch knot represented in FIG. 1 and 2, other pre-knotted displaceable knots can also be used, e.g. a Melzer and Bueβ-style open knot or an open Roeder knot.

Any suture material that is useable for surgical purposes is suitable as surgical suture material. A thread or a (woven or braided) cord made from the resorbable material polydioxanone is particularly suitable for the application fields described initially.

FIGS. 3 and 4 show a simply-designed version of a surgical knot applicator of the system according to the invention for the application of knots in surgical suture material. An essentially cylindrical shaft 20 comprises a head-part 22 in the distal zone and a gripping part 24 secured thereto in the proximal zone. A hand-grip 26 is provided at the proximal end of the gripping part 24.

Arranged in the distal end-zone 30 of the head-part 22, at the distal front side 32, is an opening 34 which is designed as a bore running on the longitudinal axis of the shaft 20. The opening 34 is enclosed by an annular shoulder 36 on the distal front side 32. The shaft 20 is preferably sloped in the distal end-zone 30 onto the periphery of the annular shoulder 36, as shown in FIGS. 3 and 4. The diameter of the opening 34 corresponds to the external diameter of a sleeve 10, so that the sleeve 10 can be inserted there.

Arranged in the interior space 38 of the head-part 22 is a pulling-in device 40 for retracting the sleeve 10 introduced into the opening 34. The pulling-in device 40 is designed as a clamping part, mounted longitudinally displaceable, which comprises two clamping jaws 42 and 43 which can engage at the section of the sleeve 10 projecting into the interior space 38. The proximal zones of the clamping jaws 42 and 43 are connected via a spring element 44 which is biased in a way that the clamping jaws 42 and 43 lie with their outer surfaces against the wall of the interior space 38. Secured in the vicinity of the distal end of the clamping jaw 42 is an operating element 46 which is guided with a thinner cylindrical section through a longitudinal slit 48 provided in the wall of the head-part 22 and then widens into a larger gripping piece. A corresponding operating element 47, connected to the clamping jaw 43, extends through a longitudinal slit 49. To pull the sleeve 10 which has been inserted into the opening 34 back into the interior space 38, the surgeon must press the operating elements 46 and 47 in the direction of the arrows E, so that the clamping jaws 42 and 43 move towards each other and grip the proximal section of the sleeve 10. He can then, when the operating elements 46 and 47 are pressed, displace the pulling-in device 40 in proximal direction. If the operating elements 46 and 47 are released, the pulling-in device 40 cannot prevent an inadvertent longitudinal displacement of the sleeve 10. The diameter of the opening 34 is thus preferably matched to the external diameter of the sleeve 10 so that frictional forces must be overcome in order to displace the sleeve 10.

Arranged at the gripping part 24 is a pulling device 50 for the pulling of the free end 16 of the surgical suture material 15 which has been guided through the sleeve 10 in proximal direction. The pulling device 50 contains a sliding sleeve 52 which is mounted longitudinally displaceable on the cylindrical shaft zone of the gripping part 24. Two gripping pieces 54 and 55 are attached in the vicinity of the proximal end of the sliding sleeve 52. Located at the distal end of the sliding sleeve 52 is a ratchet 56 which engages with a stop pawl 57 in a toothed rack 58 running in longitudinal direction on the cylindrical shaft zone of the gripping part 24. While the stop pawl 57 sits at the end of a lever arm of the ratchet 56, which is designed as a lever, the other lever arm is designed as a release lever 60. The teeth of the toothed rack 58 and the stop pawl 57 are matched to each other in such a way that the pulling device 50 can be displaced in the direction of the arrows Z, while a locking effect is produced in the opposite direction. In order to release the ratchet 56, e.g. when the pulling device 50 is to be moved back in distal direction, the release lever 60 must be pressed against an elastic force onto the gripping part 24, as a result of which the stop pawl 57 lifts off from the toothed rack 58.

As represented in FIGS. 3 and 4, the surgical suture material 15 is guided through the interior space 11 of the sleeve 10 which has been inserted into the opening 34, through the interior space 38 of the head-part 22 (and past the spring element 44) and finally through a channel 64 which runs on the longitudinal axis of the shaft 20, until it passes via an opening 66 provided at the gripping part 24 through a bore 68 arranged at the sliding sleeve 52 into the external space. There, the free end 16 of the surgical suture material 15 is fixed with the help of an eccentric lever 62 at the pulling device 50. Through movement of the gripping pieces 54 and 55 in the direction of the arrows Z, the free end 16 is thus pulled in proximal direction, as a result of which the suture produced with the surgical suture material 15 and the displaceable knot are pulled tight.

The version of the surgical knot applicator represented in FIGS. 3 and 4 is of simple design, in order to make clear the basic principle, namely pulling back a sleeve 10 inserted into the opening 34 into the interior space 38, during which operation the pre-knotted displaceable knot 18 comes to rest against the shoulder 36, and moving the free end 16 in proximal direction in order thereby to pull tight the suture and sliding knot. The individual details of the surgical knot applicator, i.e. the pulling-in device, the pulling device, the manner of securing the free end 16 of the surgical suture material 15 to the pulling device 50, the design of the grips, etc., can be differently designed. It is particularly advantageous if the pulling device is provided with a device for limiting the pulling force which is preferably adjustable to a pre-set maximum pulling force. In this case, it is ensured that the surgical suture material 15 cannot tear and the suture is pulled tight with a pre-set force. The device for limiting the pulling force can for example comprise an adjustable, pneumatic pressure cylinder.

The mode of action of the system according to the invention for the application of knots in surgical suture material is summarized once again in the following:

Firstly, a pre-knotted surgical suture means 1 matched to the proposed operation is removed from its sterile packaging. If the free end 16 of the surgical suture material 15 is provided with a surgical needle 17, a suture can created in conventional manner. The sleeve 10 with the pre-knotted displaceable knot 18 can lie in the vicinity of the later final position of the knot. Alternatively, the proximal zone of the sleeve 10 can already be inserted in the opening 34 of the surgical knot applicator 2. After the suture has been completed apart from the application of the knot 18, the needle 17 is cut off and the free end 16 of the surgical suture material 15 is introduced, through the sleeve 10 which has been inserted in the opening 34 of the knot applicator 2, into the interior space 38 of the head-part 22, which can happen e.g. with the help of a separate gripping instrument. This situation is represented in FIGS. 2 and 3, although in FIG. 3 (and also in FIG. 4) all that is shown of the suture material 15 is the part-zone with the knot 18 and also the part-zone with the free end 16, but not, on the other hand, the part-zone used for the suture or ligature. After it has emerged at the proximal end 12 of the sleeve 10, the free end 16 of the surgical suture material 15 is threaded past the spring element 44, then through the channel 64 and via the opening 66 and the bore 68 as far as the eccentric lever 62, where it is clamped fast by means of the eccentric lever 62 at the pulling device 50.

The surgeon can now pull back the sleeve 10 by means of the pulling-in device 40 in proximal direction, to which end he must press the operating elements 46 and 47 together in the direction of the arrows E and then move them in proximal direction. The knot 18 then lays itself against the shoulder 36. When the sleeve 10 has fully entered the head-part 22, see FIG. 4, the knot 18 slides over onto the surgical suture material 15. With the help of the distal end-zone 30, the surgeon can direct the knot 18 to its final position, align it and press it on. To pull the suture and the knot 18 tight, the free end 16 of the surgical suture material 15 must be moved in proximal direction, i.e. in the direction of the arrows Z. The surgeon can carry this out by pulling on the gripping pieces 54 and 55. The ratchet 56 with the stop pawl 57 engaging at the toothed rack 58 prevents the surgical suture material from loosening again. FIG. 4 shows a situation in which the pulling device 50 is largely displaced in proximal direction. After completion of the suture, the surgeon presses on the release lever 60 in order to be able to move the pulling device 50 somewhat in distal direction again, so that a piece of the surgical suture material 15 emerges again from the opening 34 at the knot 18. If he then severs the suture material in the vicinity of the opening 34, a sufficiently long piece remains in the area of the knot 18 to prevent a loosening of the knot.

We claim:

1. A device for applying a pre-knotted surgical suture, comprising:

a tube having a proximal end, a distal end, and a longitudinal passage therethrough, said tube having an inner surface and an outer surface and an outer diameter;

a surgical suture, said suture tied into a knot about the outer surface of the tube, said suture having a free end;

an applicator cylinder having a proximal end and a distal end, and an interior surface and an exterior surface, said cylinder having a longitudinal passage therethrough for receiving the tube and the free end of the suture;

an end piece mounted to the distal end of the cylinder, said end piece having a proximal end and a distal end, said end piece sloped toward its distal end, and said end piece additionally having a longitudinal passage therethrough in communication with the longitudinal passage of the cylinder, wherein the duameter of the end piece corresponds to the outer diameter of the tube;

means for pulling the tube into the longitudinal passage of the cylinder, said means comprising a clamping part mounted longitudinally displaceable in the longitudinal passage of the cylinder, said clamping part comprising a pair of opposed clamping jaws connected by a biasing spring such that the jaws are biased outwardly against the interior surface of the cylinder, and an operating element extending outwardly from each jaw through a slit in the cylinder; and, means for pulling the free end of the suture through the longitudinal passages of the cylinder and the end piece, said means comprising an elongated gripping part extending from the proximal end of the cylinder, the gripping part having a longitudinal passage for receiving the free end of the suture, said passage in communication with the longitudinal passage of the cylinder, a sliding sleeve mounted to the griping part said sleeve having a transverse hole for receiving a suture, a lever mounted to the sleeve next to the transverse hole for engaging the free end of the suture, a tooth rack extending from the gripping part and a pawl mounted to the sliding sleeve for engaging the tooth rack, wherein an adjustable pneumatic pressure cylinder is mounted to the gripping part and the sleeve for adjusting the pulling force.

* * * * *